United States Patent [19]

Hamlow et al.

[11] 3,965,167

[45] June 22, 1976

[54] CRYSTALLINE AMMONIUM N-ACETYL-L-CYSTEINATE AND MUCOLYTIC PROCESS

[75] Inventors: Eugene Emanuel Hamlow; Tellis Alexander Martin, both of Evansville, Ind.

[73] Assignee: Mead Johnson & Company, Evansville, Ind.

[22] Filed: Feb. 3, 1972

[21] Appl. No.: 223,352

[52] U.S. Cl. .............................. 260/534 S; 424/315
[51] Int. Cl.² .................................... C07C 101/04
[58] Field of Search .................. 260/534 S; 424/319

[56] References Cited
UNITED STATES PATENTS 3,091,569   5/1963   Sheffner .............................. 424/319
3,647,834   3/1972   Martin ............................. 260/429.9

OTHER PUBLICATIONS

Martin et al., J. Med. Chem., 11, 625, 1968.

Primary Examiner—Joseph E. Evans
Attorney, Agent, or Firm—Robert H. Uloth; Robert E. Carnahan

[57] ABSTRACT

The ammonium salt of N-acetyl-L-cysteine is a relatively non-hygroscopic crystalline solid which renders it particularly useful for administration by insufflation in the treatment of bronchopulmonary disease. It is of use in a mucolytic process wherein bronchopulmonary mucus is contacted with solid ammonium N-acetyl-L-cysteinate utilizing only the energy of the inspiratory action of the inhaler.

1 Claim, No Drawings

CRYSTALLINE AMMONIUM N-ACETYL-L-CYSTEINATE AND MUCOLYTIC PROCESS

BACKGROUND OF THE INVENTION

This invention deals with a therapeutic process of the drug, bio-affecting and body treating composition type. More particularly, it is concerned with the crystalline ammonium salt of N-acetyl-L-cysteine and its use in a process for effecting mucolysis of pulmonary secretions.

N-acetyl-L-cysteine is a known pharmaceutical and has been used with considerable success as a mucolytic agent, refer to U.S. Pat. No. 3,091,569. It has also been described as being of value in ameliorating inflammatory conditions in mammals (U.S. Pat. No. 3,591,686) and in permanent deformation of human hair (U.S. Pat. No. 3,242,052). The use of N-acetyl-L-cysteine in the treatment of pathological disorders in the respiratory system such as cystic fibrosis is a well-developed medical practice. N-acetyl-L-cysteine is also of value in the treatment of chronic bronchopulmonary disease including chronic emphysema, emphysema with bronchitis, chronic asthmatic bronchitis, tuberculosis, bronchiectasis, primary amyloidosis of the lung and in the treatment of acute bronchopulmonary diseases such as pneumonia, bronchitis, tracheobronchitis. The patents cited hereinabove disclose the preparation of various salts of N-acetyl-L-cysteine by neutralization with suitable alkaline-reacting substances such as sodium hydroxide, ammonium hydroxide or the like. The salts are prepared in situ and are not isolated or characterized. Certain salts of N-acetyl-L-cysteine such as the sodium salt and the like have been isolated and characterized by T. A. Martin, et al., *Journal Medicinal Chemistry*, 11, 625 (1968).

For mucolytic purposes N-acetyl-L-cysteine has been administered heretofore by nebulization, direct application, or intratracheal instillation in the form of a solution of the sodium salt. The use of finely divided solid N-acetyl-L-cysteine for inhalation, i.e. insufflation, via a dispenser in which the N-acetyl-L-cysteine is dispersed into an air stream by fluidization technique wherein the principal source of energy is the inspiratory action of the inhaler is described in U.S. Pat. No. 3,634,582. However, administration of N-acetyl-L-cysteine by this method is not entirely satisfactory in that it produces severe coughing and irritation.

SUMMARY OF THE INVENTION

This invention is concerned with crystalline N-acetyl-L-cysteine ammonium salt and its use in a mucolytic process which comprises topically contacting mucus on a mucous membrane in an animal with ammonium N-acetyl-L-cysteinate. More particularly, it is concerned with a process for effecting mucolysis of pulmonary secretions wherein crystalline ammonium N-acetyl-L-cysteinate in the form of micronized particles or ultra-fine powder is administered by insufflation utilizing only the energy of the inspiratory action of the inhaler.

Whenever a medicament is administered by insufflation for topical pulmonary therapy, it is generally recognized that it is mandatory for the medicament to be of a particle size which will enable penetration to the periphery of the lungs. Up to a point, the smaller the particle size, the deeper the particle goes into the lungs and the better mucolytic action is obtained. One mechanical device which can be employed to administer ultra-fine powders by insufflation is that described in U.S. Pat. No. 3,518,992. For this oral inhalation device the medicament is supplied in a sealed two-piece hard gelatin capsule containing one complete dose. It is notable that the medicament itself must have certain physical properties in order to be of routine value for oral inhalation therapy and particularly for use in the oral inhaler of U.S. Pat. No. 3,518,992. For example, the medicament must be a solid capable of being finely powdered or preferably micronized. It also must be relatively non-hygroscopic inasmuch as excessive hygroscopicity results in considerable added expense in formulating the medicament and makes it impracticable for self-medication in view of the difficulty in maintaining the necessary anhydrous conditions required for a reasonable shelf life.

We have now discovered that crystalline ammonium salt of N-acetyl-L-cysteine which has not heretofore been prepared in pure pulverulent form is particularly suited for insufflation administration employing only the energy of the inspiratory action of the inhaler. Pulverulent ammonium N-acetyl-L-cysteinate is also suited for inhalation administration by other means such as a pressurized aerosol container. Crystalline N-acetyl-L-cysteine ammonium salt can be readily micronized to provide ultra-fine powders of a uniform particle size range. Moreover, as noted below, unlike other salts of N-acetyl-L-cysteine such as the sodium, it is relatively non-hygroscopic.

Crystalline N-acetyl-L-cysteine ammonium salt is prepared by mixing approximately equi-molar amounts of ammonia or ammonium hydroxide and N-acetyl-L-cysteine in an inert solvent such as isopropanol under an inert atmosphere. It is isolated according to standard procedures such as filtration and can be crystallized from water-ethanol, water-isopropanol and the like. Crystalline N-acetyl-L-cysteine ammonium salt melts from about 147°–152°C. with decomposition and has an optical rotation of about $[\alpha]_D^{25} + 20.6°(c\ 5, H_2O)$.

While the sodium salt of N-acetyl-L-cysteine has met with considerable success in topical pulmonary therapy when administered in solution by conventional nebulizing techniques, it is unsatisfactory for routine administration by insufflation because of its hygroscopic nature. Other salts such as the potassium, magnesium and calcium are not suitable for insufflation administration because of hygroscopic properties. The following table indicates the degree of hygroscopicity of the ammonium salt of N-acetyl-L-cysteine compared with the sodium salt of T. A. Martin, et al., *J. Med. Chem.* 11, 625 (1968).

| HYGROSCOPICITY OF N-ACETYL-L-CYSTEINE SALTS | | | | |
|---|---|---|---|---|
| Salt | Relative Humidity | Time | Moisture Gain, % | Gross Observation |
| Ammonium | 15 | 7 days | −0.5 | Unchanged |
|  | 58 | 7 days | 0.14 | Unchanged |
|  | 88 | 7 days | 40.3 | Liquified |
| Sodium | 15 | 24 hr. | 3.1 | Partially liquified (48 hr.) |
|  | 58 | 24 hr. | 7.4 | Partially liquified |
|  | 88 | 24 hr. | 13.2 | Partially liquified |

The above values for moisture gain indicate that the ammonium salt is relatively non-hygroscopic compared with the sodium salt which partially liquifies after only one day at relative humidities ranging from 15 to 58%. Although the ammonium salt is hygroscopic at extremely high relative humidities (e.g. 88%), it does not demand the moisture protection required of the sodium salt which is not stable at a relative humidity as low as 15%.

Moreover, other salts disclosed by T. A. Martin, et al., such as (carboxymethyl)trimethylammonium N-acetyl-L-cysteinate and 10-(1-methyl-3-pyrrolidylmethyl)phenothiazinium N-acetyl-L-cysteinate after standing more than one year in a sealed container at normal atmospheric conditions liquify and partially decompose.

Powdered N-acetyl-L-cysteine ammonium salt was satisfactorily self-administered utilizing only the energy of the inspiratory action of the inhaler by employing the oral inhaler of U.S. Pat. No. 3,518,992 without any appreciable incidence of coughing and irritation by an adult male. In contrast, oral inhalation of N-acetyl-L-cysteine produced severe coughing and irritation.

This invention contemplates an effective dose of crystalline ammonium N-acetyl-L-cysteinate ranging from about 10 to 50 mg. administered three to six times daily. Unit doses of 10 mg., 20 mg., 30 mg., 40 mg., and 50 mg. in gelatin capsules are suitable for practicing the process of the present invention. Of course, the actual dosage employed in oral inhalation therapy will depend upon the nature and severity of the mucus blockade, the age and health of the subject under therapy, and the response observed.

The preparation of crystalline N-acetyl-L-cysteine ammonium salt is more fully described below.

A solution of concentrated ammonium hydroxide (52 ml., 0.78 mole) and 20 ml. water is added in 10 minutes to a stirred mixture of N-acetyl-L-cysteine (114.2 g., 0.7 mole) in 1.2 liters of isopropanol under an atmosphere of nitrogen. During the addition the mixture thickens and the temperature increases to 35°C. The mixture is stirred overnight, collected and washed with isopropanol to yield 110 g. (87%) of product having a melting point of 156°–158°C. (dec.) (uncorr.). Crystallization of this product from water-isopropanol with cooling to −10°C. provides analytically pure N-acetyl-L-cysteine ammonium salt, M.P. 147.5°–150°C. (dec.) (corr.); $[\alpha]_D^{25} + 20.6°(c\ 5, H_2O)$.

Anal. Calculated for $C_5H_8NO_3S \cdot NH_4$ (percent): C,33.30; H,6.71; N,15.54; SH,18.34. Found (percent): C,33.53; H,6.67; N,15.52; SH,18.23.

N-acetyl-L-cysteine ammonium salt can also be obtained by modification of the above procedure as follows. About 6.5 ml. of concentrated ammonium hydroxide is added slowly to a stirred mixture of N-acetyl-L-cysteine (16.3 g., 0.1 mole) in 100 ml. of water. The pH of the mixture should be 7 at the end of the addition. The solvent is allowed to evaporate and the white residue thus obtained when dried to constant weight at 45°C. in vacuo over phosphorous pentoxide provides a quantitative yield (18 g.,) of analytically pure ammonium N-acetyl-L-cysteinate, M.P. 148°–150°C. (dec.), $[\alpha]_D^{25} + 20.3°(c\ 5, H_2O)$.

Analysis. Found (percent): C,33.48; H,6.53; N,15.28; SH,18.13. Spectral data are in accord with the structural features of the ammonium salt of N-acetyl-L-cysteine.

The nuclear magnetic resonance spectrum of this substance measured in trifluoroacetic acid with tetramethylsilane as reference exhibits the following characteristics.

NMR CHARACTERISTICS OF AMMONIUM N-ACETYL-L-CYSTEINATE

| Chemical Shift (ppm) | Relative Area | Multiplicity (J Value) | Structural Feature |
|---|---|---|---|
| 1.72 | 1 | triplet (9.3 Hz) | SH |
| 2.47 | 3 | singlet | acetyl |
| 3.23 | 2 | multiplet | $CH_2$ |
| 5.15 | 1 | multiplet | CH |
| 6.75 | 4 | triplet (54.0 Hz)[a] | $NH_4^+$ |
| 8.16 | 1 | doublet (8.0 Hz) | NHCO |

[a] $H^1$–$N^{14}$ coupling

Ammonium N-acetyl-1-cysteinate exhibits infrared absorption maxima (cm.$^{-1}$) in KBr corresponding to the indicated band assignments as follows: 3330,NH(amide); 3060,$NH_4^+$; 2540,SH; 1655,CO(amide); 1580,$COO^-$and secondary amide II; 1420 and 1400,$NH_4^+$.

While particular embodiments of this invention are described above, it will be understood by those skilled in the art that the invention is not to be limited thereto since other modifications may be made without departing from the spirit and scope of the appended claims.

What is claimed is:

1. Crystalline ammonium salt of N-acetyl-L-cysteine.

* * * * *